(12) United States Patent
Mikami et al.

(10) Patent No.: US 8,278,479 B2
(45) Date of Patent: Oct. 2, 2012

(54) METHOD FOR PRODUCING OPTICALLY ACTIVE FLUORINE-CONTAINING CARBONYL-ENE PRODUCT

(75) Inventors: Koichi Mikami, Tokyo (JP); Kohsuke Aikawa, Tokyo (JP); Akihiro Ishii, Saitama (JP); Kaori Mogi, Fujimino (JP); Takashi Ootsuka, Fujimino (JP)

(73) Assignees: Central Glass Company, Limited, Ube-shi (JP); Tokyo Institute of Technology, Tokyo (JP)

( * ) Notice: Subject to any disclaimer, the term of this patent is extended or adjusted under 35 U.S.C. 154(b) by 369 days.

(21) Appl. No.: 12/519,959

(22) PCT Filed: Dec. 18, 2007

(86) PCT No.: PCT/JP2007/074290
§ 371 (c)(1),
(2), (4) Date: Jun. 18, 2009

(87) PCT Pub. No.: WO2008/078601
PCT Pub. Date: Jul. 3, 2008

(65) Prior Publication Data
US 2009/0312574 A1    Dec. 17, 2009

(30) Foreign Application Priority Data

Dec. 26, 2006 (JP) ................. 2006-350616
Feb. 27, 2007 (JP) ................. 2007-047530
Apr. 17, 2007 (JP) ................. 2007-108681

(51) Int. Cl.
*C07C 69/732* (2006.01)
(52) U.S. Cl. .................................... 560/183
(58) Field of Classification Search ............. None
See application file for complete search history.

(56) References Cited

U.S. PATENT DOCUMENTS
6,344,454 B1    2/2002    Lehmann et al.

FOREIGN PATENT DOCUMENTS
JP        2002-502385 A     1/2002
WO        WO 03/018191 A1   3/2003

OTHER PUBLICATIONS

Evans et al, Journal of the American Chemical Society, C2-Symmetric Copper (II) Complexes as Chiral Lewis Acids. Catalytic Enantioselective Carbonyl-Ene Reactions with Glyoxalate and Pyruvate Esters, 2000, 122, pp. 7936-7943.*
Kohsuke Aikawa et al., "Asymmetric catalysis of ene reactions with trifluoropyruvate catalyzed by dicationic palladium (II) complexes", Tetrahedron Letters, vol. 45, (2004) pp. 183-185.
Koichi Mikami et al., "Enantiodiscrimination and Enantiocontrol of Neutral and Cationic $Pt^{II}$ Complexes Bearing the *Tropos* Biphep Ligand: Application to Asymmetric Lewis Acid Catalysis", Angew. Chem. Int. Ed., vol. 44 (2005) pp. 7257-7260.
Simon Doherty et al., "Asymmetric Platinum Group Metal-Catalyzed Carbonyl-Ene Reactions: Carbon-Carbon Bond Formation versus Isomerization", J. Org. Chem, vol. 71 (2006) pp. 9751-9764.
Koichi Mikami et al., "Enantioselective catalysis of carbonyl-ene and Friedel-Crafts reactions with trifluoropyruvate by 'naked' palladium (II) complexes with SEGPHOS ligands", Tetrahedron: Asymmetry, vol. 15 (2004) pp. 3885-3889.
International Search Report dated Jan. 29, 2008 with partial English translation (Three (3) pages).
Chinese Office Action with English Translation dated Apr. 17, 2012 (nine (9) pages).
European Search Report dated Jan. 18, 2012 (six (6) pages).

* cited by examiner

*Primary Examiner* — Paul A Zucker
(74) *Attorney, Agent, or Firm* — Crowell & Moring LLP

(57) ABSTRACT

An optically active, fluorine-containing carbonyl-ene product is produced by reacting a fluorine-containing α-ketoester with an alkene in the presence of a transition metal complex having an optically active ligand. There are Mode 1 of conducting this reaction in the absence of reaction solvent, Mode 2 of conducting this reaction in a solvent that is low in relative dielectric constant, and Mode 3 of conducting this reaction in a halogenated hydrocarbon-series solvent. In each of these three modes, it is possible to produce the optically active, fluorine-containing carbonyl-ene product with low cost.

10 Claims, No Drawings

METHOD FOR PRODUCING OPTICALLY ACTIVE FLUORINE-CONTAINING CARBONYL-ENE PRODUCT

TECHNICAL FIELD

The present invention relates to a method for producing an optically active, fluorine-containing, carbonyl-ene product, which is an important intermediate of medicines and agricultural chemicals.

BACKGROUND OF THE INVENTION

An optically active, fluorine-containing, carbonyl-ene product, which is the target of the present invention, is an important intermediate of medicines and agricultural chemicals. As publicly known techniques relating to the present invention, there are disclosed methods of reacting ethyl trifluoropyruvate with various alkenes in the presence of a transition metal complex having an optically active ligand (Non-patent Publications 1-4).

Non-patent Publication 1: Tetrahedron Letters (UK), 2004, Vol. 45, p. 183-185.
Non-patent Publication 2: Tetrahedron Asymmetry (UK), 2004, Vol. 15, p. 3885-3889
Non-patent Publication 3: Angew. Chem. Int. Ed. (Germany), 2005, Vol. 44, p. 7257-7260
Non-patent Publication 4: J. Org. Chem. (US) 2006, browsable on the Internet (Simon Doherty, Julian G. Knight et al., Asymmetric Platinum Group Metal-Catalyzed Carbonyl-Ene Reactions: Carbon-Carbon Bond Formation versus Isomerization)

SUMMARY OF THE INVENTION

It is an object of the present invention to provide a low-cost production process of an optically active, fluorine-containing, carbonyl-ene product, which is an important intermediate of medicines and agricultural chemicals. In the methods of Non-patent Publications 1-4, it has been necessary to use high-price asymmetric catalysts by about 5 mol % in order to achieve high catalytic activity [satisfactory asymmetric induction and yield (conversion)]. How the amount of a high-price asymmetric catalyst used can be reduced is the key to produce an optically active, fluorine-containing, carbonyl-ene product with low cost. It has been necessary to find out a reaction condition that can maintain high catalytic activity even if the amount of asymmetric catalyst used is reduced. In Non-patent Publications 1-4, studies for finding out such reaction condition have almost not been conducted. Therefore, it has not been possible to produce an optically active, fluorine-containing, carbonyl-ene product with low cost.

As a result of an eager study to solve the above-mentioned task, the present inventors have found out that activity of asymmetric catalyst is greatly influenced by the type and the usage of the reaction solvent to be used. With this, we have reached the present invention. The invention of the present application includes the following three modes.

[Mode 1: A Mode of Reacting in the Absence of Reaction Solvent]

The inventors have found out useful findings that, when a fluorine-containing α-ketoester represented by formula [1] is reacted with an alkene represented by formula [2] to synthesize an optically active, fluorine-containing, carbonyl-ene product represented by formula [3], it is possible to conduct the reaction with high optical purity and good yield in the presence of a transition metal complex having an optically active ligand and in the absence of reaction solvent (e.g., Examples 2 and 7-20). We have also found out that, even if the amount of a high-price asymmetric catalyst used is greatly reduced, the optically active, fluorine-containing, carbonyl-ene product can be obtained with high optical purity and good yield (e.g., Examples 10 and 14-15).

[Mode 2: A Mode of Reacting in a Solvent that is Low in Relative Dielectric Constant]

The inventors have found out that the optically active, fluorine-containing, carbonyl-ene product can be obtained with high optical purity and good yield, under a condition that the amount of a high-price asymmetric catalyst used has greatly been reduced, by using a reaction solvent that is relatively weak in coordination ability to metal complex and that is 5.0 or less in relative dielectric constant $\in_r$, particularly a hydrocarbon series reaction solvent, too (e.g., a comparison between Examples 1, 3, and 21-28 and Comparative Examples 1-13). Although toluene is cited as an unfavorable reaction solvent in Non-patent Publication 4, it has been found out to be a particularly preferable reaction solvent in a reaction between ethyl trifluoropyruvate and isobutene, which is a preferable example of the present invention.

[Mode 3: A Mode of Reacting in a Halogenated Hydrocarbon-Series Solvent]

The inventors have found out that the reaction can preferably be conducted, even if it is a halogenated hydrocarbon-series reaction solvent, which is relatively strong in coordination ability, by limiting its usage and by conducting the reaction under a high concentration condition (e.g., a comparison between Examples 4-6 and Comparative Examples 1-3 and 9). We have also found out that, even if the amount of a high-price asymmetric catalyst used is greatly reduced, the optically active, fluorine-containing, carbonyl-ene product can be obtained with high optical purity and good yield.

That is, the present invention includes the following first to eighth methods and provides a method for producing an optically active, fluorine-containing, carbonyl-ene product with low cost that is suitable for large-scale production. The following first to third methods, the fourth to seventh methods, and the eighth method respectively correspond to the above-mentioned Mode 1, Mode 2, and Mode 3.

According to the present invention, there is provided a method (first method) for producing an optically active, fluorine-containing, carbonyl-ene product represented by formula [3]

[Chemical Formula 3]

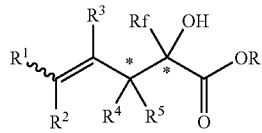

[3]

[in the formula, Rf represents a perfluoroalkyl group, R represents an alkyl group, each of $R^1$, $R^2$, $R^3$, $R^4$ and $R^5$ independently represents a hydrogen atom, alkyl group, substituted alkyl group, aromatic ring group, or substituted aromatic ring group, * represents an asymmetric carbon (it is, however, not an asymmetric carbon in case that $R^4$ and $R^5$ are the same substituents), and wave line represents an E configuration or Z configuration in geometrical configuration of the double bond] by reacting a fluorine-containing α-ketoester represented by formula [1]

[Chemical Formula 1]

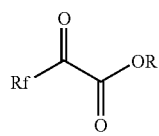

[1]

[in the formula, Rf and R respectively represent the same substituents as above] with an alkene represented by formula [2]

[Chemical Formula 2]

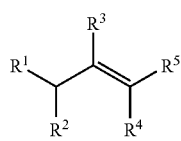

[2]

[in the formula, each of $R^1$, $R^2$, $R^3$, $R^4$ and $R^5$ independently represents the same substituent as above] in the presence of a transition metal complex having an optically active ligand and in the absence of reaction solvent.

The first method may be a method (second method) for producing optically active, trifluorocarbonyl-ene product represented by formula [6]

[Chemical Formula 6]

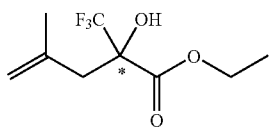

[6]

[in the formula, * represents an asymmetric carbon] by reacting ethyl trifluoropyruvate represented by formula [4]

[Chemical Formula 4]

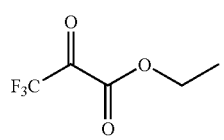

[4]

with isobutene represented by formula [5]

[Chemical Formula 5]

[5]

in the presence of 0.0005 moles or less of a bivalent cationic transition metal complex having an optically active ligand relative to 1 mole of the ethyl trifluoropyruvate represented by formula [4] and in the absence of reaction solvent.

The second method may be a method (third method) for producing (R)-trifluorocarbonyl-ene product represented by formula [7]

[Chemical Formula 9]

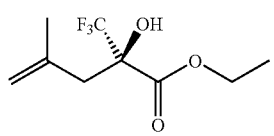

[7]

by reacting ethyl trifluoropyruvate represented by formula [4]

[Chemical Formula 7]

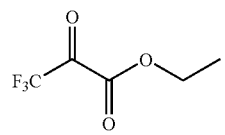

[4]

with isobutene represented by formula [5]

[Chemical Formula 8]

[5]

in the presence of 0.0003 moles or less of a bivalent cationic palladium complex having an optically active ligand relative to 1 mole of the ethyl trifluoropyruvate represented by formula [4] and in the absence of reaction solvent.

According to the present invention, there is provided a method (fourth method) for producing an optically active, fluorine-containing, carbonyl-ene product represented by formula [3]

[Chemical Formula 12]

[3]

[in the formula, Rf represents a perfluoroalkyl group, R represents an alkyl group, each of $R^1$, $R^2$, $R^3$, $R^4$ and $R^5$ independently represents a hydrogen atom, alkyl group, substituted alkyl group, aromatic ring group, or substituted aromatic ring group, * represents an asymmetric carbon (it is, however, not an asymmetric carbon in case that $R^4$ and $R^5$ are the same substituents), and wave line represents an E configuration or Z configuration in geometrical configuration of the double bond] by reacting a fluorine-containing α-ketoester represented by formula [1]

[Chemical Formula 10]

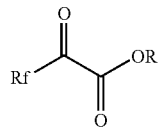
[1]

[in the formula, Rf and R respectively represent the same substituents as above] with an alkene represented by formula [2]

[Chemical Formula 11]

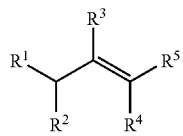
[2]

[in the formula, each of $R^1$, $R^2$, $R^3$, $R^4$ and $R^5$ independently represents the same substituents as above] in the presence of 0.001 moles or less of a transition metal complex having an optically active ligand relative to 1 mole of the fluorine-containing α-ketoester represented by formula [1] and in the presence of a reaction solvent that is 5.0 or less in relative dielectric constant $\in_r$.

The fourth method may be a method (fifth method) for producing an optically active, fluorine-containing, carbonyl-ene product represented by formula [3]

[Chemical Formula 15]

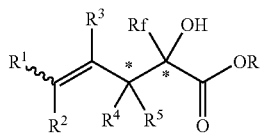
[3]

[in the formula, Rf represents a perfluoroalkyl group, R represents an alkyl group, each of $R^1$, $R^2$, $R^3$, $R^4$ and $R^5$ independently represents a hydrogen atom, alkyl group, substituted alkyl group, aromatic ring group, or substituted aromatic ring group, * represents an asymmetric carbon (it is, however, not an asymmetric carbon in case that $R^4$ and $R^5$ are the same substituents), and wave line represents an E configuration or Z configuration in geometrical configuration of the double bond] by reacting a flourine-containing α-ketoester represented by formula [1]

[Chemical Formula 13]

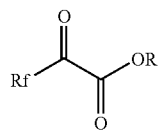
[1]

[in the formula Rf and R respectively represent the same substituents as above] with an alkene represented by formula [2]

[Chemical Formula 14]

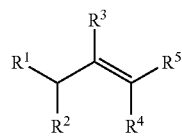
[2]

[in the formula, each of $R^1$, $R^2$, $R^3$, $R^4$ and $R^5$ independently represents the same substituent as above] in the presence of 0.001 moles or less of a transition metal complex having an optically active ligand relative to 1 mole of the fluorine-containing α-ketoester represented by formula [1] and in the presence of a hydrocarbon-series reaction solvent.

The fifth method may be a method (sixth method) for producing optically active, trifluorocarbonyl-ene product represented by formula [6]

[Chemical Formula 18]

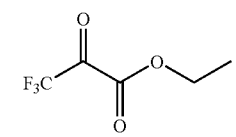
[6]

[in the formula, * represents an asymmetric carbon] by reacting ethyl trifluoropyruvate represented by formula [4]

[Chemical Formula 16]

[4]

$F_3C$ with isobutene represented by formula [5]

[Chemical Formula 17]

[5]

in the presence of 0.0005 moles or less of a bivalent cationic transition metal complex having an optically active ligand relative to 1 mole of the ethyl trifluoropyruvate represented by formula [4] and in the presence of an aromatic hydrocarbon-series reaction solvent.

The sixth method may be a method (seventh method) for producing (R)-trifluorocarbonyl-ene product represented by formula [7]

[Chemical Formula 21]

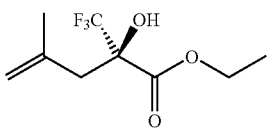

[7]

by reacting ethyl trifluoropyruvate represented by formula [4]

[Chemical Formula 19]

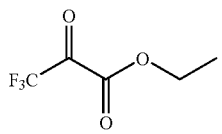

[4]

with isobutene represented by formula [5]

[Chemical Formula 20]

[5]

in the presence of 0.0003 moles or less of a bivalent cationic palladium complex having an optically active ligand relative to 1 mole of the ethyl trifluoropyruvate represented by formula [4] and in the presence of toluene as reaction solvent.

According to the present invention, there is provided a method (eighth method) for producing an optically active, fluorine-containing, carbonyl-ene product represented by formula [3]

[Chemical Formula 24]

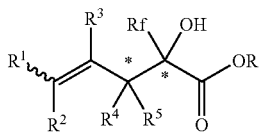

[3]

[in the formula, Rf, R, $R^1$, $R^2$, $R^3$, $R^4$ and $R^5$ represent the same substituents as above, * represents an asymmetric carbon (it is, however, not an asymmetric carbon in case that $R^4$ and $R^5$ are the same substituents), and wave line represents an E configuration or Z configuration in geometrical configuration of the double bond] by reacting a fluorine-containing α-ketoester represented by formula [1]

[Chemical Formula 22]

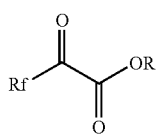

[1]

[in the formula, Rf represents a perfluoroalkyl group, and R represents an alkyl group] with an alkene represented by formula [2]

[Chemical Formula 23]

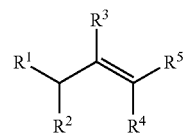

[2]

[in the formula, each of $R^1$, $R^2$, $R^3$, $R^4$ and $R^5$ independently represents a hydrogen atom, alkyl group, substituted alkyl group, aromatic ring group, or substituted aromatic ring group] in the presence of a transition metal complex having an optically active ligand and in the presence of less than 1.0 L (liter) of a halogenated hydrocarbon-series reaction solvent relative to 1 mole of the fluorine-containing α-ketoester represented by formula [1].

DETAILED DESCRIPTION

In the production method of the present invention, it is possible to not only solve the problem (high production cost due to the use of a high-price asymmetric catalyst in large amount) of Non-patent Publications 1-4, but also reduce the usage of methylene chloride, which is limited in industrial use as a reaction solvent, (a reaction solvent frequently used in Non-patent Publications 1-4). Alternatively, the reaction can also be conducted without using it at all. Even under such condition, it is possible to produce the target product with high yield and high asymmetric yield, and there occurs no production of impurities that are difficult of separation. Particularly in the case of using no reaction solvent, it is possible to remarkably improve productivity of the reaction and operability of the post-treatment.

A method of the present invention for producing an optically active, fluorine-containing, carbonyl-ene product is explained in detail. Firstly, matters common to Mode 1 to Mode 3 are explained.

As perfluoroalkyl group of fluorine-containing α-ketoester represented by formula [1], it is possible to cite one having a carbon atom number of 1-6. One having a carbon atom number of 3 or greater can take a straight-chain or branch. As alkyl group of fluorine-containing α-ketoester represented by formula [1], it is possible to cite one having a carbon atom number of 1-6. One having a carbon atom number of 3 or greater can take a straight-chain or branch.

Of the fluorine-containing α-ketoester, one is preferable, in which Rf is a trifluoromethyl group, and R is a methyl group or ethyl group, and which can easily be produced and can industrially be used. It is preferable for producing the optically active, fluorine-containing, carbonyl-ene product.

As alkyl groups of alkene represented by formula [2], it is possible to cite those having a carbon atom number of 1-6. Those having a carbon atom number of 3 or greater can take a straight-chain or branch. Two alkyl groups can also form by a covalent bond a cyclopentane ring, cyclohexane ring, cycloheptane ring, cyclopentene ring, cyclohexene ring, cycloheptene ring, or the like.

As substituted alkyl group of alkene represented by formula [2], a hydroxyl-group's protector or the like can substitute in the alkyl group. As the protecting group of the hydroxyl group, it is possible to suitably use those mentioned in Protective Groups in Organic Synthesis, Third Edition, 1999, John Wiley & Sons, Inc. Of those, benzyl group and t-butyldiphenylsilyl group are preferable.

As aromatic ring group of alkene represented by formula [2], it is possible to cite aromatic hydrocarbon groups, such as phenyl group, and the like.

As substituted aromatic ring group of alkene represented by formula [2], a halogen atom, such as fluorine atom or chlorine atom, a lower alkyl group, such as methyl group, or the like can substitute in the aromatic ring group. The aromatic ring group and the alkyl group can also form a covalent bond.

Of the alkene, 1,1-disubstituted olefin, which is high in reactivity, is preferable. Isobutene is preferable, in view of importance of the obtained product as a medicine intermediate. We have made it clear that the production method of the present invention is a single-step, very excellent method, in view of that a method for industrially producing optically active, trifluorocarbonyl-ene product represented by formula [6], particularly (R)-trifluorocarbonyl-ene product represented by formula [7], has been limited in conventional techniques to a two-step method of synthesizing the corresponding racemate and conducting optical resolution.

The usage of alkene represented by formula [2] is not particularly limited. Normally, the use of 0.7 moles or greater is enough, the use of 0.8-10 moles is preferable, and particularly the use of 0.9-7 moles is more preferable, relative to 1 mole of fluorine-containing α-ketoester represented by formula [1].

As the transition metal complex having an optically active ligand, it is possible to cite a bivalent cationic complex represented by formula [8]

[Chemical Formula 25]

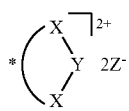

[in the formula, X-*-X represents the following optically active SEGPHOS derivative (chemical formula 26), optically active BINAP derivative (chemical formula 27), optically active BIPHEP derivative (chemical formula 28), optically active P-Phos derivative (chemical formula 29), optically active PhanePhos derivative (chemical formula 30), optically active 1,4-Et$_2$-cyclo-C$_6$H$_8$-NUPHOS (chemical formula 31) or optically active BOX derivative (chemical formula 32), or the like, Y represents Ni, Pd, Pt or Cu, and Z represents SbF$_6$, ClO$_4$, BF$_4$, OTf (Tf; CF$_3$SO$_2$), AsF$_6$, PF$_6$, or B(3,5-(CF$_3$)$_2$C$_6$H$_3$)$_4$]

[Chemical Formula 26]

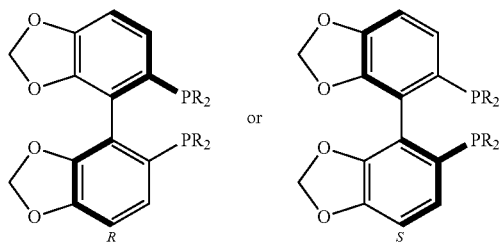

optically active SEGPHOS derivative

SEGPHOS; R = C$_6$H$_5$
DM-SEGPHOS; R = 3,5-(CH$_3$)$_2$C$_6$H$_3$
DTBM-SEGPHOS; R = 4-CH$_3$O-3,5-(t-C$_4$H$_9$)$_2$C$_6$H$_2$

[Chemical Formula 27]

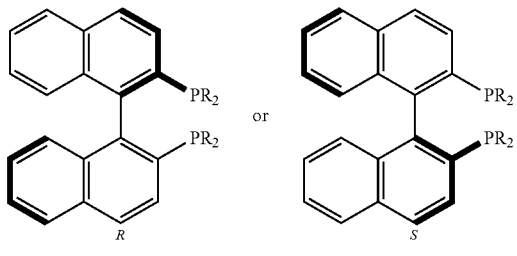

optically active BINAP derivative

BINAP; R = C$_6$H$_5$
Tol-BINAP; R = 4-CH$_3$C$_6$H$_4$
Xyl-BINAP; R = 3,5-(CH$_3$)$_2$C$_6$H$_3$

[Chemical Formula 28]

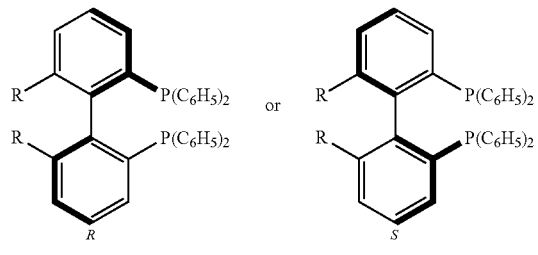

optically active BIPHEP derivative

BIPHEP; R = H
BIPHEMP; R = CH$_3$
MeO-BIPHEP; R = CH$_3$O

[Chemical Formula 29]

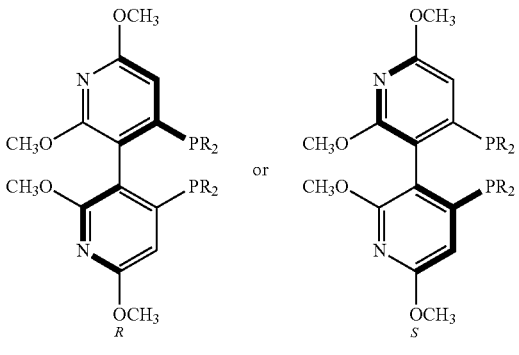

optically active P-Phos derivative

P-Phos; R = C$_6$H$_5$
Tol-P-Phos; R = 4-CH$_3$C$_6$H$_4$
Xyl-P-Phos; R = 3,5-(CH$_3$)$_2$C$_6$H$_3$

[Chemical Formula 30]

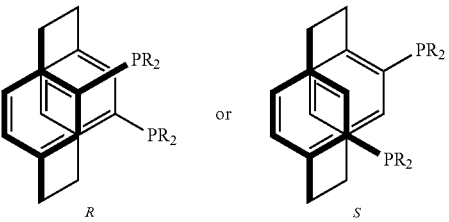

optically active PhanePhos derivative

PhanePhos; R = C$_6$H$_5$
Tol-PhanePhos; R = 4-CH$_3$C$_6$H$_4$
Xyl-PhanePhos; R = 3,5-(CH$_3$)$_2$C$_6$H$_3$ -continued

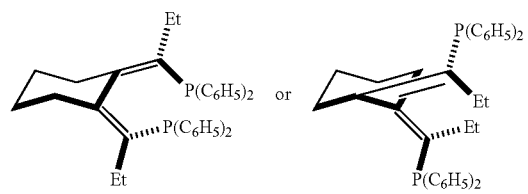

Et = C₂H₅
1,4-Et₂-cyclo-C₆H₈-NUPHOS

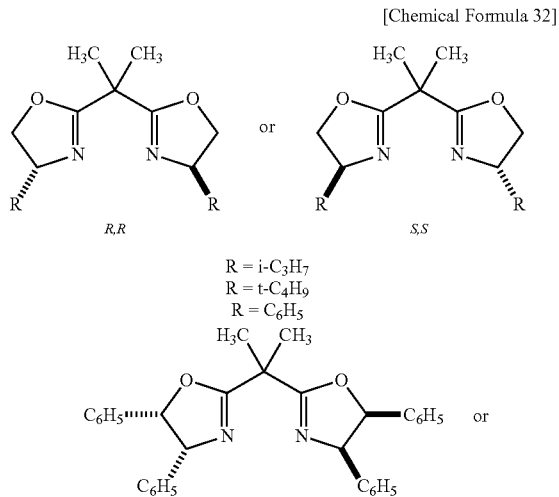

R = i-C₃H₇
R = t-C₄H₉
R = C₆H₅ optically active BOX derivative
or BINOL-Ti complex represented by formula [9]

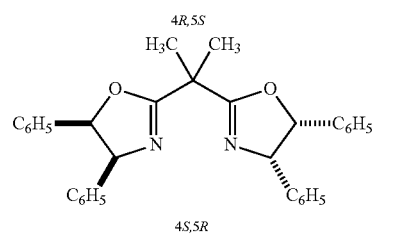

[9]

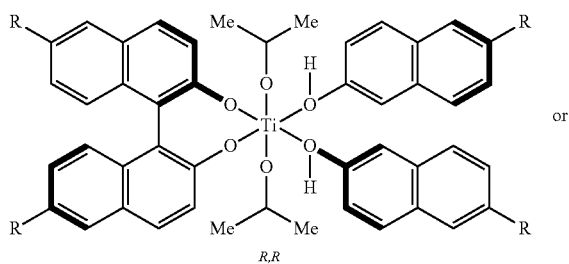

[in the formula, R represents a hydrogen atom, chlorine atom, bromine atom, iodine atom or trifluoromethyl group, and Me represents a methyl group] or the like. Of these, the bivalent cationic complex is preferable, and particularly the bivalent cationic palladium complex is more preferable (As the optically active ligand, representative ones are cited, and it is possible to suitably use those mentioned in CATALYTIC ASYMMETRIC SYNTHESIS, Second Edition, 2000, Wiley-VCH, Inc. As Z, $SbF_6$, $BF_4$, OTf, and $B(3,5\text{-}(CF_3)_2C_6H_3)_4$ are preferable. Particularly, $SbF_6$, OTf, and $B(3,5\text{-}(CF_3)_2C_6H_3)_4$ are more preferable).

These complexes can be prepared by publicly known methods (for example, Non-patent Publications 1-4, J. Am. Chem. Soc. (US), 1999, Vol. 121, p. 686-699, nature (UK), 1997, Vol. 385, p. 613-615, etc.), and, besides an isolated complex (e.g., Reference Examples 1-2; isolated), the use without isolation following a previous preparation in the reaction system is also possible (e.g., Methods C to D-2 and F of Examples; in situ). As these complexes, it is also possible to use ones to which water or an organic solvent such as acetonitrile is coordinated (solvation) [since the usage of asymmetric catalyst is extremely small, the solvent coordinated to the complex can be neglected, and it is not treated (not converted) as reaction solvent]. As in situ complex, a bivalent cationic complex having a fluorine-containing α-ketoester as a ligand is preferable, which is represented by formula [10]

[Chemical Formula 34]

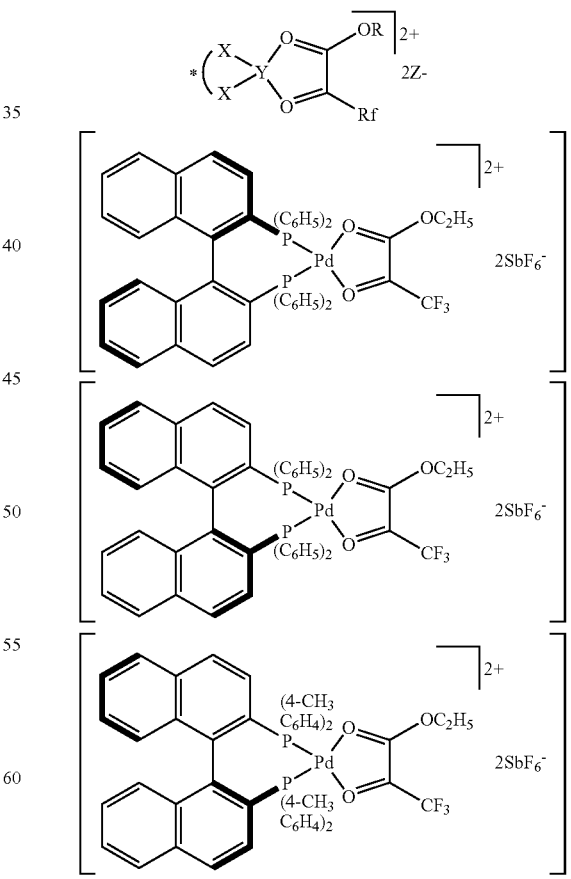

[in the formula, X-*-X, Y and Z represent the same ones as those of formula [8], Rf and R represent the same ones as those of formula [1]], which can easily be prepared by novel Method D, D-2 or F with no necessity of using reaction solvent at all, and which is extremely high in activity of asymmetric catalyst.

Furthermore, it is possible in some cases to use a cationic binuclear complex, too, which is represented by formula [11]

[Chemical Formula 35]

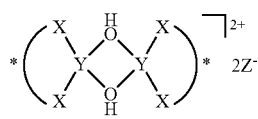

[11]

[in the formula, X-*-X, Y and Z represent the same ones as those of formula [8]], similar to the bivalent cationic complex represented by formula [8].

It is possible to suitably use stereochemistry [(R), (S), (R,R), (S,S), etc.] of the optically active ligand in accordance with stereochemistry of the target optically active, fluorine-containing, carbonyl-ene product. In view of importance of the obtained product as a medicine intermediate, stereochemistry of the optically active ligand that gives a (R)-fluorine-containing carbonyl-ene product is preferable. It suffices to suitably set optical purity of the optically active ligand in accordance with the target optical purity of the optically active, fluorine-containing carbonyl-ene product. Normally, it suffices to use 95% ee (enantiomeric excess) or greater, the use of 97% ee or greater is preferable, and particularly the use of 99% ee or greater is more preferable.

Of these optically active ligands, BINAP derivatives are preferable, since both enantiomers can be obtained with the lowest price, and since activity upon converted into an asymmetric catalyst is also extremely high. BINAP and Tol-BINAP are preferable, and particularly BINAP is more preferable.

As the usage of the transition metal complex having an optically active ligand, it suffices to use 0.001 moles or less, the use of 0.0005 moles or less is preferable, and particularly the use of 0.0003 moles or less is more preferable, relative to 1 mole of fluorine-containing α-ketoester represented by formula [1], to gain the maximum of the effect of the present invention (to have a production with a cost as low as possible). Of course, it is also possible to conduct it with a usage of more than 0.001 moles in no consideration of the production cost. In Mode 2 in the present invention, however, 0.001 moles or less of the asymmetric catalyst (transition metal complex) is used relative to 1 mole of fluorine-containing α-ketoester represented by formula [1].

The reaction temperature is not particularly limited. Normally, it suffices to conduct it in a range of −60 to +60° C. It is preferable to conduct it in a range of −50 to +50° C. Particularly, it is more preferable to conduct it in a range of −40 to +40° C. Furthermore, in the reaction between ethyl trifluoropyruvate and isobutene, which is a preferable example of the present invention, sometimes the reaction proceeds, even if asymmetric catalyst does not exist, and there exists a reaction pathway to give a racemate (lowering optical purity of the target optically active trifluorocarbonyl-ene product), and sometimes isobutene remaining in the reaction-terminated liquid generates side reactions (lowering chemical purity of the target optically active trifluorocarbonyl-ene product). Therefore, in the present reaction, normally it suffices to conduct it in a range of −60 to +30° C. It is preferable to conduct it in a range of −50 to +20° C. Particularly, it is more preferable to conduct it in a range of −40 to +10° C.

The order of adding the raw material substrates, asymmetric catalyst, and the reaction solvent is not limited to [Method A] to [Method F] mentioned in Examples. In the case of adding alkene at last that is one of the raw material substrates, it is possible to obtain an optically active fluorine-containing carbonyl-ene product with high optical purity by gradually adding it while controlling it to the above reaction temperature or lower.

The reaction time is not particularly limited. Normally, it suffices to conduct it within 24 hours. It depends on the raw material substrates, asymmetric catalyst, the reaction conditions, etc. Therefore, it is preferable to monitor the condition of the reaction progress by analytical means such as gas chromatography, thin-layer chromatography, liquid chromatography, or nuclear magnetic resonance (NMR) and judge the time when the raw material substrates have almost disappeared as being the end point.

Next, an explanation is conducted on each matter of Mode 1 to Mode 3 of the present invention.

Firstly, Mode 1 is explained. Mode 1 of the present invention is a method of conducting the target reaction in the absence of reaction solvent.

Herein, to conduct the reaction in the absence of reaction solvent means that the reaction solvent does substantially not exist in the reaction system (neat condition). Specifically, it refers to a condition of the reaction solvent being less than 0.10 L, relative to 1 mol of fluorine-containing α-ketoester represented by formula [1]. A condition of less than 0.05 L is preferable, and particularly a condition of less than 0.01 L is more preferable. More typically, it suffices to conduct the reaction without adding liquid compound from the outside of the system on one's own initiative, besides the reaction substrates and the transition metal complex. It is the most preferable mode of Mode 1.

Due to that the reaction solvent does substantially not exist in the reaction system, not only productivity of the reaction improves remarkably, but also waste liquid derived from the reaction solvent is not discharged in the post-treatment. Therefore, it is extremely advantageous from the viewpoint of reducing burden on the environment, too. Thus, it is one of important findings of the present invention that the target reaction proceeds with high yield and high optical purity even in the absence of reaction solvent.

Furthermore, the inventors have found out that the reaction proceeds well by the existence of an asymmetric catalyst in an extremely small amount under such no solvent condition. By these findings, it has become possible to conduct the target reaction of the present invention economically remarkably advantageously as compared with the past.

In Mode 1, a method for producing optically active, trifluorocarbonyl-ene product represented by formula [6] by reacting ethyl trifluoropyruvate represented by formula [4] with isobutene represented by formula [5] in the presence of 0.0005 moles or less of a bivalent cationic transition metal complex having an optically active ligand relative to 1 mole of ethyl trifluoropyruvate represented by formula [4] and in the absence of reaction solvent is particularly preferable in terms of usefulness of the product, the raw material availability, that the reaction can preferably be conducted, etc.

In Mode 1, a method for producing (R)-trifluorocarbonyl-ene product represented by formula [7] by reacting ethyl trifluoropyruvate represented by formula [4] with isobutene represented by formula [5] in the presence of 0.0003 moles or less of a bivalent cationic palladium complex having an optically active ligand relative to 1 mole of ethyl trifluoropyruvate represented by formula [4] and in the absence of reaction solvent is still more preferable due to that the reaction can be conducted still more economically advantageously, etc.

Next, Mode 2 is explained. Mode 2 of the present invention is one in which the target reaction is conducted in the presence of a reaction solvent that is 5.0 or less in relative dielectric constant $\in_r$.

Herein, as a reaction solvent that is 5.0 or less in relative dielectric constant $\in_r$, it is possible to cite aliphatic hydrocarbon series such as n-pentane, n-hexane, cyclohexane, and n-heptane; aromatic hydrocarbon series such as benzene, toluene, xylene, and mesitylene; ethers such as diethyl ether, t-butyl methyl ether, and 1,4-dioxane (however, tetrahydrofuran is excluded); etc [in the present invention, it refers to the value of relative dielectric constant $\in_r$ of the reaction solvent at around 20° C. (20-25° C.)]. Of these, hydrocarbon series is preferable, particularly aromatic hydrocarbon series is more preferable, and furthermore toluene is extremely preferable. These reaction solvents that are 5.0 or less in relative dielectric constant $\in_r$ can be used alone or in combination.

The usage of the reaction solvent that is 5.0 or less in relative dielectric constant $\in_r$ is not particularly limited. Normally, it suffices to use 3.0 L or less, the use of 2.0 L or less is preferable, and particularly the use of 1.0 L or less is more preferable, relative to 1 mole of fluorine-containing α-ketoester represented by formula [1].

To conduct the reaction in the presence of a reaction solvent (reaction solvent that is 5.0 or less in relative dielectric constant $\in_r$) refers to a condition in which 0.10 L or greater is used relative to 1 mole of fluorine-containing α-ketoester represented by formula [1].

In Mode 2, it is also possible to use a mixed solvent prepared by combining a reaction solvent that is greater than 5.0 in relative dielectric constant $\in_r$ and a reaction solvent that is 5.0 or less in relative dielectric constant $\in_r$. In this case, substantially the same effect can be expected as that of the reacting in the presence of a reaction solvent that is 5.0 or less in relative dielectric constant $\in_r$, due to that coordination ability to metal complex, which is originally owned by a reaction solvent that is greater than 5.0 in relative dielectric constant $\in_r$, is weakened. For example, in case that a hydrocarbon-series reaction solvent is used in the same volume or more as that of a halogenated hydrocarbon-series reaction solvent, it is possible to obtain the target product with high optical purity and good yield by a small amount of asymmetric catalyst, even if the usage of the halogenated hydrocarbon-series reaction solvent is in 1.0 L or more relative to 1 mole of fluorine-containing α-ketoester represented by formula [1]. Therefore, in the case of mentioning a reaction solvent that is 5.0 or less in relative dielectric constant $\in_r$ in the present invention, there is also included a mixed solvent of a reaction solvent that is 5.0 or less in relative dielectric constant $\in_r$ and a reaction solvent that is greater than 5.0 in relative dielectric constant $\in_r$, the mixed solvent being such that the former has been used in the same volume or more as that of the latter.

In Mode 2, a method for producing optically active fluorine-containing carbonyl-ene product represented by formula [3] by reacting fluorine-containing α-ketoester represented by formula [1] with alkene represented by formula [2] in the presence of 0.001 moles or less of a transition metal complex having an optically active ligand relative to 1 mole of fluorine-containing α-ketoester represented by formula [1] and in the presence of a hydrocarbon-series reaction solvent is preferable, since reactivity is good.

In Mode 2, a method for producing optically active trifluorocarbonyl-ene product represented by formula [6] by reacting ethyl trifluoropyruvate represented by formula [4] with isobutene represented by formula [5] in the presence of 0.0005 moles or less of a bivalent cationic transition metal complex having an optically active ligand relative to 1 mole of ethyl trifluoropyruvate represented by formula [4] and in the presence of an aromatic hydrocarbon-series reaction solvent is particularly preferable, due to usefulness of the product, the raw material availability, that reactivity is good, etc.

In Mode 2, a method for producing (R)-trifluorocarbonyl-ene product represented by formula [7] by reacting ethyl trifluoropyruvate represented by formula [4] with isobutene represented by formula [5] in the presence of 0.0003 moles or less of a bivalent cationic palladium complex having an optically active ligand relative to 1 mole of ethyl trifluoropyruvate represented by formula [4] and in the presence of toluene as reaction solvent is still more preferable, due to usefulness of the product, the raw material availability, that reactivity is still better, etc.

Next, Mode 3 is explained. Mode 3 is one in which the reaction is conducted in the presence of less than 1.0 L of a halogenated hydrocarbon-series reaction solvent relative to 1 mole of fluorine-containing α-ketoester represented by formula [1].

Herein, as a halogenated hydrocarbon-series reaction solvent, it is possible to cite methylene chloride, chloroform, 1,2-dichloroethane, etc. Of these, methylene chloride and 1,2-dichloroethane are preferable, and particularly methylene chloride is more preferable. These halogenated hydrocarbon-series reaction solvents can be used alone or in combination. Of course, they can also be used in combination with a reaction solvent that is 5.0 or less in relative dielectric constant $\in_r$.

As the usage of a halogenated hydrocarbon-series reaction solvent, less than 1.0 L is used, the use of less than 0.7 L is preferable, and particularly the use of less than 0.5 L is more preferable, relative to 1 mole of fluorine-containing α-ketoester represented by formula [1].

In the present invention, the reacting in the presence of a halogenated hydrocarbon-series reaction solvent refers to a condition in which the halogenated hydrocarbon-series reaction solvent is used in 0.10 L or more relative to 1 mole of fluorine-containing α-ketoester represented by formula [1].

Next, the post-treatment step common to Mode 1 to Mode 3 is explained.

As the post-treatment, there is no particular limitation. It is possible to obtain the target optically active fluorine-containing carbonyl-ene product represented by formula [3] by conducting normal operations on the reaction-terminated liquid. According to need, the crude product can be purified to high purity by an operation such as activated carbon treatment, distillation, recrystallization, or column chromatography. In a reaction between ethyl trifluoropyruvate and isobutene, which is a preferable example of the present invention, it is extremely important to control side reactions by removing under low temperature isobutene remaining in the reaction-terminated liquid to the outside of the system. Therefore, in the present post-treatment, normally conducting in a range of −60 to +30° C. is enough, conducting in a range of −50 to +20° C. is preferable, and particularly conducting in a range of −40 to +10° C. is more preferable. As the manner for removal to the outside of the system, there is no particular limitation. There is preferable a method of removing it to the outside of the system by blowing inert gas such as nitrogen, argon or the like and accompanying it or a method of directly removing it from the reaction-terminated liquid under reduced pressure. Furthermore, in the present post-treatment, after isobutene is removed from the reaction-terminated liquid by the above method to a make condition where no side reaction occurs, it is possible to continuously recover (reaction solvent can also be recovered in the case of using reaction solvent) the target product by fractional distillation (according to need, it can be conducted under reduced pressure). Therefore, it is possible to remarkably improve operability of the post-treatment (an example of preferable post-treatments). Furthermore, as a method of controlling side reactions of isobutene remaining in the reaction-terminated liquid, there is also effective a method of adding to the reaction-terminated liquid a reaction solvent that is greater than 5.0 in relative dielectric constant ∈$_r$, such as dimethylsulfoxide, N,N-dimethylformamide, acetonitrile, propionitrile, acetone, methylene chloride, tetrahydrofuran, ethyl acetate or the like, a phosphine ligand such as triphenylphosphine, 1,2-bis(diphenylphosphino)ethane or the like, etc.

In the present invention, recovery and reuse of asymmetric catalyst are possible, and method of recovery and reuse is not particularly limited. There is preferable a method where, in the above-mentioned preferable examples of the post-treatment, asymmetric catalyst is recovered as a distillation residue, and then it is reused by adding again ethyl trifluoropyruvate and isobutene, or a method where asymmetric catalyst [according to need, which has been allowed to stand under cooling or to which a poor solvent (e.g., aliphatic hydrocarbon-series solvent or the like) has been added] precipitated from the reaction-terminated liquid is recovered by decantation, filtration or the like, and then it is reused similar to the above. Particularly, the latter is more preferable, since it can be applied to the recovery of an asymmetric catalyst that is thermally unstable. In the case of the former, an asymmetric catalyst that is thermally unstable can also be recovered, under a condition that a relatively high activity is maintained, by conducting a distillation under reduced pressure by controlling the bath temperature at 70° C. or lower (preferably 60° C. or lower, and more preferably 50° C. or lower).

EXAMPLES

Embodiments of the present invention are specifically explained by examples, but the present invention is not limited to these examples. Furthermore, reference examples and comparative examples are mentioned in order to supplementarily explain examples. Regarding the concentration indication of reaction solvent of Table 1 and Table 3, the case of using reaction solvent in 4.0 L, 2.0 L, 1.0 L, 0.5 L, 0.25 L, 0.2 L, 0.167 L, or 0.125 L relative to 1 mole of fluorine-containing α-ketoester represented by formula [1] is respectively represented by 0.25M, 0.5M, 1.0M, 2.0M, 4.0M, 5.0M, 6.0M, or 8.0M.

Reference Example 1

A reaction container was charged with 85.7 mg (0.109 mmol, 1 eq) of (S)-SEGPHOS-PdCl$_2$ represented by the following formula

[Chemical Formula 36]

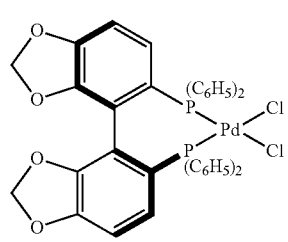

followed by replacement with argon. 5.4 ml of acetone (50 ml/1 mmol of (S)-SEGPHOS-PdCl$_2$), 5.1 mg (0.283 mmol, 2.6 eq) of water, and 82.4 mg (0.240 mmol, 2.2 eq) of AgSbF$_6$ were added, followed by stirring for 1 hour at room temperature.

The preparation-terminated liquid was subjected to Celite filtration, followed by concentration under reduced pressure, adding methylene chloride to the concentration residue, and allowing it to stand for 1 day. The methylene chloride solution was subjected again to Celite filtration, followed by concentration under reduced pressure, vacuum drying, and recrystallizing the dried residue from methylene chloride and n-hexane, thereby obtaining 92.0 mg (solid, yield 69%) of (S)-SEGPHOS-Pd($^{2+}$)(OH$_2$)$_2$.2SbF$_6^-$ (isolated) represented by the following formula.

[Chemical Formula 37]

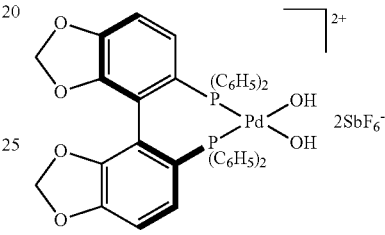

Reference Example 2

A reaction container was charged with 160.0 mg (0.200 mmol, 1 eq) of (R)-BINAP-PdCl$_2$ represented by the following formula

[Chemical Formula 38]

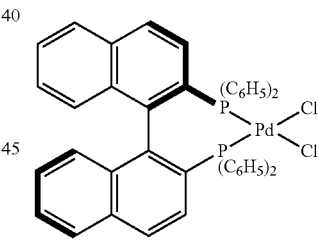

followed by replacement with nitrogen. 10.0 ml of acetone (50 ml/mmol of (R)-BINAP-PdCl$_2$), 9.4 mg (0.520 mmol, 2.6 eq) of water, and 151.2 mg (0.440 mmol, 2.2 eq) of AgSbF$_6$ were added, followed by stirring for 1 hour at room temperature.

The preparation-terminated liquid was subjected to Celite filtration, followed by concentration under reduced pressure, adding 5.0 ml of methylene chloride to the concentration residue, and allowing it to stir for all night. The methylene chloride solution was subjected again to Celite filtration, followed by concentration under reduced pressure, vacuum drying, and recrystallizing (stirring for all night) the dried residue from 2.0 ml of methylene chloride and 15.0 ml of n-hexane, thereby obtaining 213.2 mg (a yellow-color solid, yield 86%) of (R)-BINAP-Pd($^{2+}$)(OH$_2$)$_2$.2SbF$_6^-$ (isolated) represented by the following formula.

[Chemical Formula 39]

Examples 1-28 and Comparative Examples 1-13

General production methods A to F of Examples and Comparative Examples are shown, and these results are put together in Tables 1-3. Furthermore, representative post-treatment operations are also described.

[Method A]

A reaction container was charged with (S)-SEGPHOS-Pd($^{2+}$)(OH$_2$)$_2$·2SbF$_6^-$ (isolated: meaning an isolated one. Hereinafter, the same.) represented by the following formula

[Chemical Formula 40]

followed by replacement with argon (in the case of using reaction solvent, it was added at this stage). It was cooled down to a predetermined, substrate-addition temperature and charged with ethyl trifluoropyruvate represented by the following formula

[Chemical Formula 41]

and isobutene represented by the following formula

[Chemical Formula 42]

followed by stirring at a predetermined reaction temperature for a predetermined reaction time.

The reaction-terminated liquid was subjected to post-treatment, thereby obtaining (R)-trifluorocarbonyl-ene product represented by the following formula.

[Chemical Formula 43]

[Method B]

A reaction container was charged with (R)-BINAP-Pd($^{2+}$)(OH$_2$)$_2$·2SbF$_6^-$ (isolated) represented by the following formula

[Chemical Formula 44]

followed by replacement with nitrogen. At room temperature, ethyl trifluoropyruvate represented by the following formula

[Chemical Formula 45]

was added (in the case of adding reaction solvent, it was added at this stage), followed by cooling down to a predetermined, substrate-addition temperature, adding isobutene represented by the following formula

[Chemical Formula 46]

and stirring at a predetermined reaction temperature for a predetermined reaction time.

The reaction-terminated liquid was subjected to post-treatment, thereby obtaining (S)-trifluorocarbonyl-ene product represented by the following formula.

[Chemical Formula 47]

[Method C]

A reaction container was charged with (R)-BINAP-PdCl$_2$ (1 eq) represented by the following formula

[Chemical Formula 48]

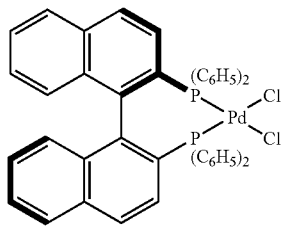

and AgSbF$_6$ (2.2 eq), followed by vacuum drying and replacement with nitrogen. To the dried residue, acetone (200 ml/1 mmol of (R)-BINAP-PdCl$_2$) and water (2.6 eq) were added, followed by stirring at room temperature for 1 hr.

The preparation-terminated liquid was subjected to concentration under reduced pressure and vacuum drying, thereby obtaining (R)-BINAP-Pd($^{2+}$)(OH$_2$)$_2$.2SbF$_6^-$ (in situ) represented by the following formula

[Chemical Formula 49]

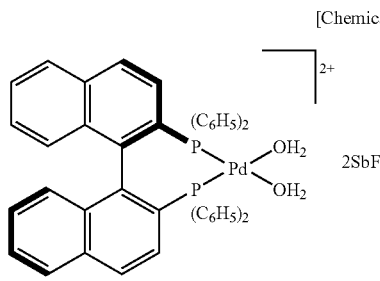

(a yellow-color solid, yield was assumed to be 100%).

The reaction container was replaced with nitrogen and charged at room temperature with ethyl trifluoropyruvate represented by the following formula

[Chemical Formula 50]

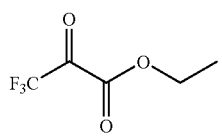

followed by cooling down to a predetermined, substrate-addition temperature, adding isobutene represented by the following formula

[Chemical Formula 51]

and stirring at a predetermined reaction temperature for a predetermined reaction time.

The reaction-terminated liquid was subjected to post-treatment, thereby obtaining (S)-trifluorocarbonyl-ene product represented by the following formula.

[Chemical Formula 52]

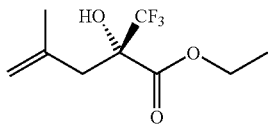

[Method D]

A reaction container was charged with (R)-BINAP-PdCl$_2$ (1 eq) represented by the following formula

[Chemical Formula 53]

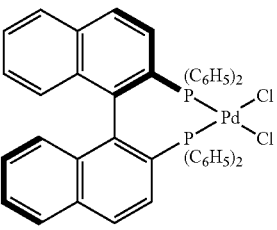

followed by replacement with nitrogen. At room temperature, ethyl trifluoropyruvate represented by the following formula

[Chemical Formula 54]

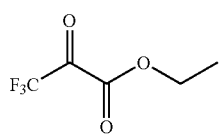

and AgSbF$_6$ (2.2 eq) were added, and stirring was conducted at room temperature for 1 hr.

As the preparation-terminated liquid, an ethyl trifluoropyruvate solution of (R)-BINAP-Pd($^{2+}$)— CF$_3$COCO$_2$C$_2$H$_5$.2SbF$_6^-$ (in situ) represented by the following formula

[Chemical Formula 55]

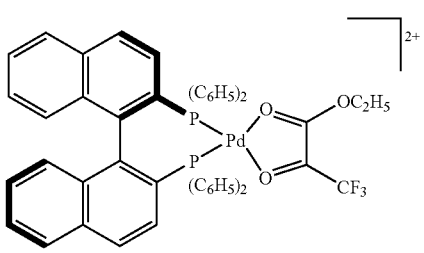

was obtained (a yellow-color suspension, yield was assumed to be 100%).

It was cooled down to a predetermined, substrate-addition temperature, followed by adding isobutene represented by the following formula

[Chemical Formula 56]

and stirring at a predetermined reaction temperature for a predetermined reaction time.

The reaction-terminated liquid was subjected to post-treatment, thereby obtaining (S)-trifluorocarbonyl-ene product represented by the following formula.

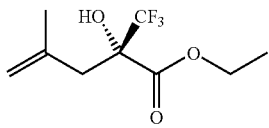

[Chemical Formula 57]

[Method D-2]

In Method D, in place of (R)-BINAP-PdCl$_2$, (S)-BINAP-PdCl$_2$ represented by the following formula

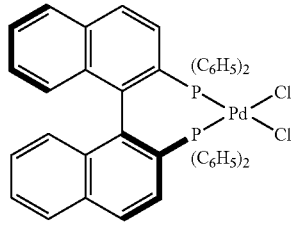

[Chemical Formula 58]

was used to conduct it similarly, thereby obtaining (R)-trifluorocarbonyl-ene product represented by the following formula.

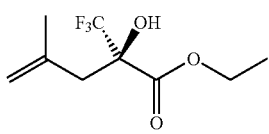

[Chemical Formula 59]

[Method E]

A reaction container was charged with (S)-SEGPHOS-Pd ($^{2+}$)(OH$_2$)$_2$·2SbF$_6^-$ (isolated) represented by the following formula

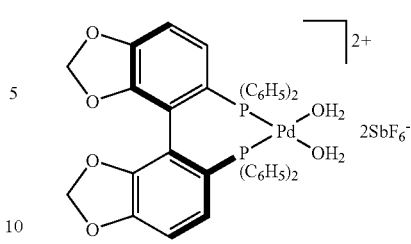

[Chemical Formula 60]

followed by replacement with argon. It was cooled down to a predetermined, substrate-addition temperature, followed by adding ethyl trifluoropyruvate represented by the following formula

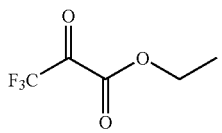

[Chemical Formula 61]

and methylenecyclohexane represented by the following formula

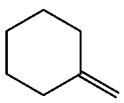

[Chemical Formula 62]

and stirring at a predetermined reaction temperature for a predetermined reaction time.

The reaction-terminated liquid was subjected to post-treatment, thereby obtaining (R)-trifluorocarbonyl-ene product represented by the following formula.

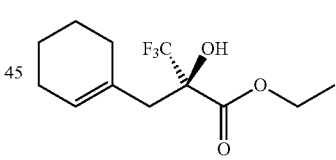

[Chemical Formula 63]

[Method F]

A reaction container was charged with (S)-Tol-BINAP-PdCl$_2$ (1 eq) represented by the following formula

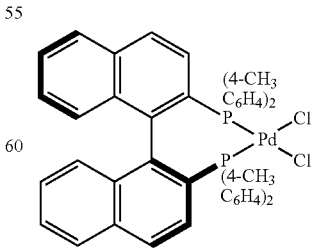

[Chemical Formula 64]

followed by replacement with nitrogen. At room temperature, ethyl trifluoropyruvate represented by the following formula

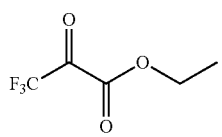

[Chemical Formula 65]

and AgSbF$_6$ (2.2 eq) were added, followed by stirring at room temperature for 1.5 hours.

As the preparation-terminated liquid, an ethyl trifluoropyruvate solution of (S)-Tol-BINAP-Pd($^{2+}$)—CF$_3$COCO$_2$C$_2$H$_5$·2SbF$_6^-$ (in situ) represented by the following formula

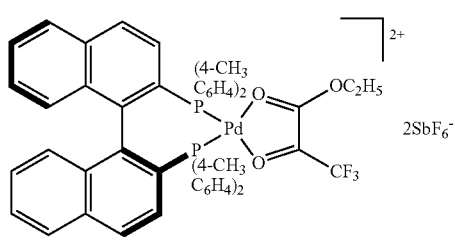

[Chemical Formula 66]

was obtained (an orange-color to yellow-color suspension, yield was assumed to be 100%).

It was cooled down to a predetermined, substrate-addition temperature, followed by adding isobutene represented by the following formula

[Chemical Formula 67]

and stirring at a predetermined reaction temperature for a predetermined reaction time.

The reaction-terminated liquid was subjected to post-treatment, thereby obtaining (R)-trifluorocarbonyl-ene product represented by the following formula.

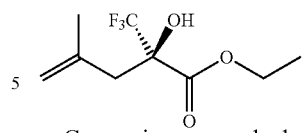

[Chemical Formula 68]

Conversion was calculated from the following formula after measuring gas chromatography of Condition-1 and Condition-2. Relative areal values of A, B and C were determined on the basis of areal value of C (in the case of Condition-2, the total areal value of R configuration and S configuration) in each measurement condition (Condition-1; comparison between areal value of B and areal value of C, Condition-2; comparison between areal value of A and areal value of C).

[Numerical Formula 1]

$$\text{Conversion (\%)} = \frac{\text{(Relative areal value of } C\text{)}}{\text{(Relative areal value of } A + \text{Relative areal value of } B + \text{Relative areal value of } C\text{)}} \times 100$$

$$\begin{bmatrix} A; \text{ ethyl trifluoropyruvate} \\ B; \text{ ethyl trifluoropyruvate hydrate} \\ C; \text{ optically active trifluorocarbonyl-ene product} \end{bmatrix}$$

Conversion of Comparative Example 7 was, however, calculated by the following formula from the measurement result of Condition-1, since peaks of propionitrile of the reaction solvent and ethyl trifluoropyruvate overlapped with each other in the measurement of Condition-2.

[Numerical Formula 2]

$$\text{Conversion of Comparative Example 7 (\%)} = \frac{\text{Areal value of } C}{\text{Areal value of } B + \text{Areal value of } C} \times 100$$

Furthermore, conversions of Examples 1, 2 and 12 and Comparative Example 1 were determined by $^1$H-NMR.

Optical purity was calculated by the following formula after measuring gas chromatography of Condition-2.

[Numerical Formula 3]

$$\text{Optical purity of } R \text{ configuration (\% } ee\text{)} = \frac{\text{Areal value of } R \text{ configuration} - \text{Areal value of } S \text{ configuration}}{\text{Areal value of } R \text{ configuration} + \text{Areal value of } S \text{ configuration}} \times 100$$

or

[Numerical Formula 4]

$$\text{Optical purity of } S \text{ configuration (\% } ee\text{)} = \frac{\text{Areal value of } S \text{ configuration} - \text{Areal value of } R \text{ configuration}}{\text{Areal value of } S \text{ configuration} + \text{Areal value of } R \text{ configuration}} \times 100$$

Condition-1)
Column; DB-5 (I. D. 0.25 mm×30 m, film 0.25 μm), carrier gas; He, flow rate; 163 kPa (column inlet pressure), temperature condition; 50° C. (5 minutes retention)→10° C./min (temperature rise)→250° C. (5 minutes retention)/total 30 minutes, injection; 250° C., detector (FID); 250° C., split ratio; 50, retention time; ethyl trifluoropyruvate hydrate for about 6 minutes, and optically active trifluorocarbonyl-ene product (derived from isobutene) for about 9 minutes.

Condition-2)
Column; Cyclodex-β (I. D. 0.25 mm×30 m, film 0.25 μm), carrier gas; He, flow rate; 163 kPa (column inlet pressure), temperature condition; 50° C. (5 minutes retention)→10° C./min (temperature rise)→150° C. (10 minutes retention)/total 25 minutes, injection; 200° C., detector (FID); 200° C., split ratio; 50, retention time; ethyl trifluoropyruvate for about 2 minutes, and optically active trifluorocarbonyl-ene product (derived from isobutene) R configuration for 11.6 minutes and S configuration for 11.7 minutes.

Instrumental data of optically active trifluorocarbonyl-ene product (derived from isobutene) are shown. $^1$H-NMR [standard substance; $(CH_3)_4Si$, deuterated solvent; $CDCl_3$], δ ppm; 1.34 (t, 7.1 Hz, 3H), 1.78 (s, 3H), 2.58 (d, 14.0 Hz, 1H), 2.75 (d, 14.0 Hz, 1H), 3.86 (br, 1H), 4.34 (m, 2H), 4.81 (s, 1H), 4.91 (s, 1H), $^{13}$C-NMR [standard substance; $(CH_3)_4Si$, deuterated solvent; $CDCl_3$], δ ppm; 13.9, 23.9, 38.7, 63.7, 78.1 (q, $J_{C\text{-}F}$=28.7 Hz), 116.1, 123.3 (q, $J_{C\text{-}F}$=286.8 Hz), 138.7, 169.5, specific rotation [optical purity 97.9% ee(R)]; $[\alpha]^{23.7}_D$=−6.8 ($CHCl_3$, c=2.47).

TABLE 1

| Ex. | Method | F-containing α-ketoester | Alkene | Transition metal complex having an optically active ligand |
|---|---|---|---|---|
| Comp. Ex. 1 | A | ethyl trifluoropyruvate 20 mmol | isobutene 3.9eq | (S)-SEGPHOS-Pd$^{(2+)}$(OH$_2$)$_2$•2SbF$_6^-$ (isolated) 0.01 mol % |
| Ex. 1 | A | ethyl trifluoropyruvate 20 mmol | isobutene 3.9eq | (S)-SEGPHOS-Pd$^{(2+)}$(OH$_2$)$_2$•2SbF$_6^-$ (isolated) 0.01 mol % |
| Ex. 2 | A | ethyl trifluoropyruvate 20 mmol | isobutene 3.9eq | (S)-SEGPHOS-Pd$^{(2+)}$(OH$_2$)$_2$•2SbF$_6^-$ (isolated) 0.01 mol % |
| Comp. Ex. 2 | B | ethyl trifluoropyruvate 50 mmol | isobutene 2.0eq | (R)-BINAP-Pd$^{(2+)}$(OH$_2$)$_2$•2SbF$_6^-$ (isolated) 0.01 mol % |
| Comp. Ex. 3 | B | ethyl trifluoropyruvate 50 mmol | isobutene 2.0eq | (R)-BINAP-Pd$^{(2+)}$(OH$_2$)$_2$•2SbF$_6^-$ (isolated) 0.01 mol % |
| Ex. 3 | B | ethyl trifluoropyruvate 50 mmol | isobutene 2.0eq | (R)-BINAP-Pd$^{(2+)}$(OH$_2$)$_2$•2SbF$_6^-$ (isolated) 0.01 mol % |
| Ex. 4 | B | ethyl trifluoropyruvate 50 mmol | isobutene 2.0eq | (R)-BINAP-Pd$^{(2+)}$(OH$_2$)$_2$•2SbF$_6^-$ (isolated) 0.01 mol % |
| Ex. 5 | B | ethyl trifluoropyruvate 50 mmol | isobutene 2.0eq | (R)-BINAP-Pd$^{(2+)}$(OH$_2$)$_2$•2SbF$_6^-$ (isolated) 0.01 mol % |
| Ex. 6 | B | ethyl trifluoropyruvate 50 mmol | isobutene 2.0eq | (R)-BINAP-Pd$^{(2+)}$(OH$_2$)$_2$•2SbF$_6^-$ (isolated) 0.01 mol % |
| Ex. 7 | B | ethyl trifluoropyruvate 50 mmol | isobutene 2.0eq | (R)-BINAP-Pd$^{(2+)}$(OH$_2$)$_2$•2SbF$_6^-$ (isolated) 0.01 mol % |
| Ex. 8 | C | ethyl trifluoropyruvate 50 mmol | isobutene 5.0eq | (R)-BINAP-Pd$^{(2+)}$(OH$_2$)$_2$•2SbF$_6^-$ (in situ) 0.01 mol % |
| Ex. 9 | D | ethyl trifluoropyruvate 50 mmol | isobutene 2.0eq | (R)-BINAP-Pd$^{(2+)}$-CF$_3$COCO$_2$C$_2$H$_5$•2SbF$_6^-$ (in situ) 0.01 mol % |
| Ex. 10 | B | ethyl trifluoropyruvate 50 mmol | isobutene 2.0eq | (R)-BINAP-Pd$^{(2+)}$(OH$_2$)$_2$•2SbF$_6^-$ (isolated) 0.005 mol % |

| Ex. | Reaction Solvent | Substrate Addition Temp. | Reaction Temp. | Reaction Time | Conversion | Optical Purity |
|---|---|---|---|---|---|---|
| Comp. Ex. 1 | methylene chloride[1] (1.0M) | −30° C. | 0° C. | 9 hr | >99% | 0% ee |
| Ex. 1 | toluene[2] (1.0M) | −30° C. | 0° C. | 4 hr | >99% | 98% ee (R) |
| Ex. 2 | neat | −30° C. | 0° C. | 4 hr | >99% | 98% ee (R) |
| Comp. Ex. 2 | methylene chloride (0.25M) | −20° C. | −20° C. | 2 hr | 3% | 1% ee (S) |
| Comp. Ex. 3 | methylene chloride (1.0M) | −20° C. | −20° C. | 2 hr | 98% | 89% ee (S) |
| Ex. 3 | toluene (1.0M) | −20° C. | −20° C. | 2 hr | >99% | 97% ee (S) |
| Ex. 4 | methylene chloride (4.0M) | −20° C. | −20° C. | 2 hr | >99% | 96% ee (S) |
| Ex. 5 | methylene chloride (6.0M) | −20° C. | −20° C. | 2 hr | 99% | 96% ee (S) |
| Ex. 6 | methylene chloride (8.0M) | −20° C. | −20° C. | 1 hr | >99% | 97% ee (S) |
| Ex. 7 | neat | −20° C. | −20° C. | 1.5 hr | >99% | 95% ee (S) |
| Ex. 8 | neat | −30° C. | −20° C. | 2 hr | 99% | 95% ee (S) |
| Ex. 9 | neat | −20° C. | −20° C. | 1 hr | >99% | 96% ee (S) |
| Ex. 10 | neat | −20° C. | −20° C. | 2 hr | 98% | 96% ee (S) |

[1]relative dielectric constant $\epsilon_r$; 8.93 (25° C.)
[2]relative dielectric constant $\epsilon_r$; 2.379 (23° C.)

TABLE 2

| Ex. | Method | F-containing α-ketoester | Alkene | Transition metal complex having an optically active ligand |
|---|---|---|---|---|
| Ex. 11 | A | ethyl trifluoropyruvate 4 mmol | isobutene 5.0eq | (S)-SEGPHOS-Pd$^{(2+)}$(OH$_2$)$_2$•2SbF$_6^-$ (isolated) 0.1 mol % |
| Ex. 12 | A | ethyl trifluoropyruvate 20 mmol | isobutene 3.9eq | (S)-SEGPHOS-Pd$^{(2+)}$(OH$_2$)$_2$•2SbF$_6^-$ (isolated) 0.01 mol % |
| Ex. 13 | E | ethyl trifluoropyruvate 2.2 mmol | methylenecyclohexane 0.91eq | (S)-SEGPHOS-Pd$^{(2+)}$(OH$_2$)$_2$•2SbF$_6^-$ (isolated) 0.5 mol % |
| Ex. 14 | D | ethyl trifluoropyruvate 63 mmol | isobutene 2.0eq | (R)-BINAP-Pd$^{(2+)}$-CF$_3$COCO$_2$C$_2$H$_5$•2SbF$_6^-$ (in situ) 0.004 mol % |
| Ex. 15 | D | ethyl trifluoropyruvate 150 mmol | isobutene 2.0eq | (R)-BINAP-Pd$^{(2+)}$-CF$_3$COCO$_2$C$_2$H$_5$•2SbF$_6^-$ (in situ) 0.002 mol % |
| Ex. 16 | B | ethyl trifluoropyruvate 50 mmol | isobutene 5.0eq | (R)-BINAP-Pd$^{(2+)}$(OH$_2$)$_2$•2SbF$_6^-$ (isolated) 0.01 mol % |
| Ex. 17 | D-2 | ethyl trifluoropyruvate 235 mmol | isobutene 1.4eq | (S)-BINAP-Pd$^{(2+)}$-CF$_3$COCO$_2$C$_2$H$_5$•2SbF$_6^-$ (in situ) 0.01 mol % |
| Ex. 18 | D-2 | ethyl trifluoropyruvate 235 mmol | isobutene 1.1eq | (S)-BINAP-Pd$^{(2+)}$-CF$_3$COCO$_2$C$_2$H$_5$•2SbF$_6^-$ (in situ) 0.01 mol % |
| Ex. 19 | D-2 | ethyl trifluoropyruvate 470 mmol | isobutene 1.0eq | (S)-BINAP-Pd$^{(2+)}$-CF$_3$COCO$_2$C$_2$H$_5$•2SbF$_6^-$ (in situ) 0.01 mol % |
| Ex. 20 | F | ethyl trifluoropyruvate 250 mmol | isobutene 2.0eq | (S)-Tol-BINAP-Pd$^{(2+)}$-CF$_3$COCO$_2$C$_2$H$_5$•2SbF$_6^-$ (in situ) 0.01 mol % |

| Ex. | Reaction Solvent | Substrate Addition Temp. | Reaction Temp. | Reaction Time | Conversion | Optical Purity |
|---|---|---|---|---|---|---|
| Ex. 11 | neat | −30° C. | room temp.[1] | 1 hr | 98%[2] | 98% ee (R) |
| Ex. 12 | neat | −20° C. | −20° C. | 9 hr | >99% | 99% ee (R) |
| Ex. 13 | neat | −78° C. | room temp. | 1 hr | 86%[2] | 95% ee (R) |
| Ex. 14 | neat | −20° C. | −20° C. | 1 hr | 93% | 96% ee (S) |
| Ex. 15 | neat | −20° C. | −20° C. | 1 hr | 76% | 96% ee (S) |
| Ex. 16 | neat | −20° C. | −10° C. | 2 hr | >99% | 96% ee (S) |
| Ex. 17 | neat | −20° C. | −20° C. | 1 hr | 55% | 96% ee (R) |
| Ex. 18 | neat | −20° C. | −20° C. | 2 hr | 83% | 98% ee (R) |
| Ex. 19 | neat | −20° C. | −20° C. | 2 hr | 98% | 99% ee (R) |
| Ex. 20 | neat | −20° C. | −20° C. | 1 hr | >99% | 98% ee (R) |

[1] reaction for 1 hr at room temperature after reacting at −30° C. for 10 minutes
[2] isolation yield

TABLE 3

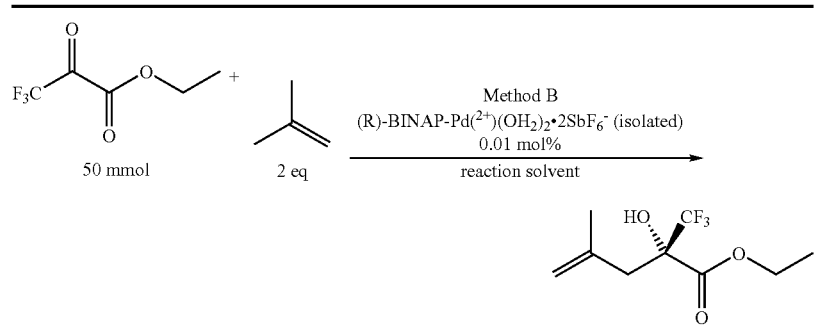

| Ex. | Reaction Solvent | Relative Dielectric Constant $\epsilon_r$[1] | Substrate Addition Temp. | Reaction Temp. | Reaction Time | Conversion | Optical Purity |
|---|---|---|---|---|---|---|---|
| Comp. Ex. 4 | dimethylsulfoxide (1.0 M) | 47.24 (20° C.) | 20° C. | 20° C. | 2 hr | 6% | 4% ee (S) |
| Comp. Ex. 5 | N,N-dimethylformamide (1.0 M) | 36.71 (25° C.) | −20° C. | −20° C. | 2 hr | <1% | 1% ee (S) |
| Comp. Ex. 6 | acetonitrile (1.0 M) | 36.64 (20° C.) | −20° C. | −20° C. | 2 hr | 1% | 1% ee (S) |
| Comp. Ex. 7 | propionitrile (1.0 M) | 29.7 (20° C.0) | −20° C. | −20° C. | 2 hr | 4% | 1% ee (S) |
| Comp. Ex. 8 | acetone (1.0 M) | 21.01 (20° C.0) | −20° C. | −20° C. | 2 hr | <1% | 8% ee (S) |

TABLE 3-continued

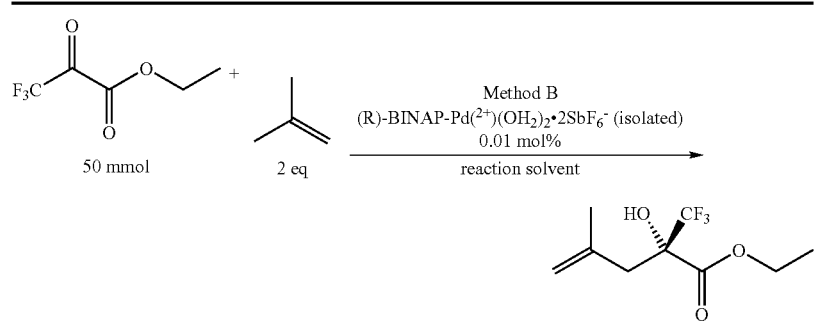

| Ex. | Reaction Solvent | Relative Dielectric Constant $\epsilon_r$[1] | Substrate Addition Temp. | Reaction Temp. | Reaction Time | Conversion | Optical Purity |
|---|---|---|---|---|---|---|---|
| Comp. Ex. 9 | methylene chloride (0.5 M) | 8.93 (25° C.) | −20° C. | −20° C. | 2 hr | 66% | 7% ee (R) |
| Comp. Ex. 10 | tetrahydrofuran (2.0 M) | 7.52 (22° C.) | −20° C. | −20° C. | 2 hr | <1% | 1% ee (R) |
| Comp. Ex. 11 | (1.0 M) | as above | −20° C. | −20° C. | 2 hr | <1% | 12% ee (S) |
| Comp. Ex. 12 | ethyl acetate (2.0 M) | 6.0814 (20° C.) | −20° C. | −20° C. | 2 hr | <1% | 23% ee (S) |
| Comp. Ex. 13 | (1.0 M) | as above | −20° C. | −20° C. | 2 hr | <1% | 11% ee (S) |
| Ex. 21 | diethyl ether (5.0 M) | 4.2666 (20° C.) | −20° C. | −20° C. | 1 hr | >99% | 97% ee (S) |
| Ex. 22 | (1.0 M) | as above | −20° C. | −20° C. | 2 hr | 93% | 97% ee (S) |
| Ex. 23 | (0.5 M) | as above | −20° C. | −20° C. | 2 hr | 91% | 97% ee (S) |
| Ex. 24 | (0.25 M) | as above | −20° C. | −20° C. | 2 hr | 48% | 97% ee (S) |
| Ex. 25 | t-butyl methyl ether (0.5 M) | unknown | −20° C. | −20° C. | 2 hr | 81% | 97% ee (S) |
| Ex. 26 | 1,4-dioxane (2.0 M) | 2.2189 (20° C.) | 0° C. | 0° C. | 2 hr | 39% | 95% ee (S) |
| Ex. 27[2] | (1.0 M) | as above | 0° C. | 0° C. | 2 hr | 16% | 92% ee (S) |
| Ex. 28 | n-hexane (1.0 M) | 1.8865 (20° C.) | −20° C. | −20° C. | 4 hr | 76% | 97% ee (S) |

[1] extracted from "Revised 5th-edition Kagaku Binran Kiso-hen II, edited by The Chemical Society of Japan, MARUZEN Co., Ltd. II-619-622" or "ORGANIC SOLVENTS; PHYSICAL PROPERTIES AND METHODS OF PURIFICATION, Fourth Edition, 1986, John Wiley & Sons, Inc."
[2] 35 mmol scale

[Post-Treatment Operation of Example 2]

The reaction-terminated liquid was directly subjected to column chromatography (silica gel, n-pentane:diethyl ether=8:1), thereby obtaining (R)-trifluorocarbonyl-ene product (derived from isobutene) in 4.433 g (a colorless, transparent liquid, yield 98%, chemical purity 99%, optical purity 98% ee).

[Post-Treatment Operation of Example 7]

Isobutene remaining in the reaction-terminated liquid was concentrated under reduced pressure at −10 to −5° C., followed by distillation under reduced pressure (bath temperature; ~+70° C.), thereby obtaining (S)-trifluorocarbonyl-ene product (derived from isobutene) in 10.90 g (a colorless, transparent liquid, yield 96%, chemical purity 99%, optical purity 95% ee).

[Post-Treatment Operation of Example 14]

Isobutene remaining in the reaction-terminated liquid was concentrated under reduced pressure at 0° C., followed by distillation under reduced pressure (bath temperature; ~50° C.), thereby obtaining (S)-trifluorocarbonyl-ene product (derived from isobutene) in 12.89 g (a colorless, transparent liquid, yield 91%, chemical purity 99%, optical purity 96% ee).

[Post-Treatment Operation of Example 21]

Isobutene and diethyl ether remaining in the reaction-terminated liquid were concentrated under reduced pressure at 0° C., followed by distillation under reduced pressure (bath temperature; ~50° C.), thereby obtaining (S)-trifluorocarbonyl-ene product (derived from isobutene) in 11.21 g (a colorless, transparent liquid, yield 99%, chemical purity >99%, optical purity 97% ee).

The invention claimed is:

1. A method for producing an optically active, fluorine-containing, carbonyl-ene product represented by formula [3]

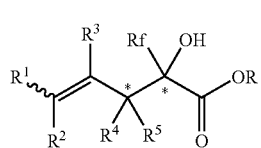

[3]

wherein Rf represents a perfluoroalkyl group,

R represents an alkyl group, each of $R^1$, $R^2$, $R^3$, $R^4$ and $R^5$ independently represents a hydrogen atom, alkyl group, substituted alkyl group, aromatic ring group, or substituted aromatic ring group,

* represents an asymmetric carbon but is not an asymmetric carbon in case that $R^4$ and $R^5$ are the same substituents, and wave line represents an E configuration or Z configuration in geometrical configuration of the double bond, the method comprising reacting a fluorine-containing α-ketoester represented by formula [1]

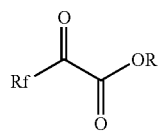

[1]

wherein Rf and R respectively represent the same substituents as above, with an alkene represented by formula [2]

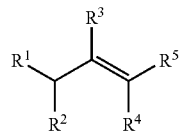

[2]

wherein each of $R^1$, $R^2$, $R^3$, $R^4$ and $R^5$ independently represents the same substituent as above, in the presence of a transition metal complex having an optically active ligand and in the absence of a reaction solvent that is different from the fluorine-containing α-ketoester and the alkene.

2. A method according to claim 1, wherein usage of the transition metal complex having the optically active ligand is 0.001 moles or less relative to 1 mole of the fluorine-containing α-ketoester represented by formula [1].

3. A method for producing optically active, trifluorocarbonyl-ene product represented by formula [6]

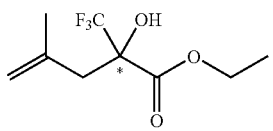

[6]

wherein * represents an asymmetric carbon, the method comprising reacting ethyl trifluoropyruvate represented by formula [4]

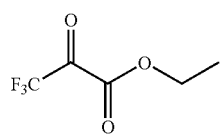

[4]

with isobutene represented by formula [5]

[5]

in the presence of 0.0005 moles or less of a bivalent cationic transition metal complex having an optically active ligand relative to 1 mole of the ethyl trifluoropyruvate represented by formula [4] and in the absence of a reaction solvent that is different from the ethyl trifluoropyruvate and the isobutene.

4. A method for producing (R)-trifluorocarbonyl-ene product represented by formula [7]

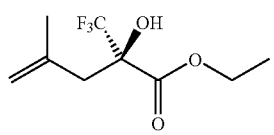

[7]

the method comprising reacting ethyl trifluoropyruvate represented by formula [4]

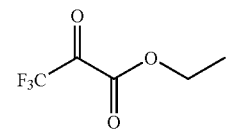

[4]

with isobutene represented by formula [5]

[5]

in the presence of 0.0003 moles or less of a bivalent cationic palladium complex having an optically active ligand relative to 1 mole of the ethyl trifluoropyruvate represented by formula [4] and in the absence of a reaction solvent that is different from the ethyl trifluoropyruvate and the isobutene.

5. A method for producing an optically active, fluorine-containing, carbonyl-ene product represented by formula [3]

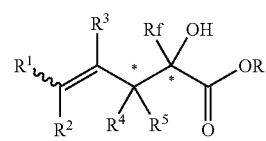

[3]

wherein Rf represents a perfluoroalkyl group,

R represents an alkyl group, each of $R^1$, $R^2$, $R^3$, $R^4$ and $R^5$ independently represents a hydrogen atom, alkyl group, substituted alkyl group, aromatic ring group, or substituted aromatic ring group,

* represents an asymmetric carbon but is not an asymmetric carbon in case that $R^4$ and $R^5$ are the same substituents, and wave line represents an E configuration or Z configuration in geometrical configuration of the double bond] by reacting a fluorine-containing α-ketoester represented by formula [1]

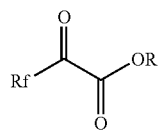

[1]

wherein Rf and R respectively represent the same substituents as above, with an alkene represented by formula [2]

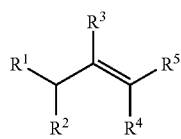

[2]

wherein each of $R^1$, $R^2$, $R^3$, $R^4$ and $R^5$ independently represents the same substituents as above, in the presence of 0.001 mole or less of a transition metal complex having an optically active ligand relative to 1 mole of the fluorine-containing α-ketoester represented by formula [1] and in the presence of a reaction solvent that is 5.0 or less in relative dielectric constant $\in_r$.

6. A method for producing an optically active, fluorine-containing, carbonyl-ene product represented by formula [3]

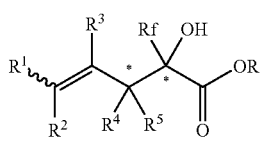

[3]

wherein Rf represents a perfluoralkyl group,
R represents an alkyl group,
each of $R^1$, $R^2$, $R^3$, $R^4$ and $R^5$ independently represents a hydrogen atom, alkyl group, substituted alkyl group, aromatic ring group, or substituted aromatic ring group,
* represents an asymmetric carbon but is not an asymmetric carbon in case that $R^4$ and $R^5$ are the same substituents, and
wave line represents an E configuration or Z configuration in geometrical configuration of the double bond the method comprising reacting a fluorine-containing α-ketoester represented by formula [1]

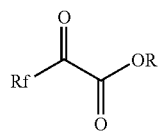

[1]

wherein Rf and R respectively represent the same substituents as above, with an alkene represented by formula [2]

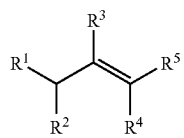

[2]

wherein each of $R^1$, $R^2$, $R^3$, $R^4$ and $R^5$ independently represents the same substituent as above, in the presence of 0.001 mole or less of a transition metal complex having an optically active ligand relative to 1 mole of the fluorine-containing α-ketoester represented by formula [1] and in the presence of a hydrocarbon-series reaction solvent.

7. A method for producing optically active, trifluorocarbonyl-ene product represented by formula [6]

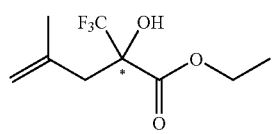

[6]

wherein * represents an asymmetric carbon the method comprising reacting ethyl trifluoropyruvate represented by formula [4]

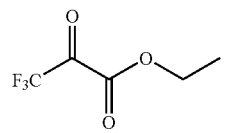

[4]

with isobutene represented by formula [5]

[5]

in the presence of 0.0005 moles or less of a bivalent cationic transition metal complex having an optically active ligand relative to 1 mole of the ethyl trifluoropyruvate represented by formula [4] and in the presence of an aromatic hydrocarbon-series reaction solvent.

8. A method for producing (R)-trifluorocarbonyl-ene product represented by formula [7]

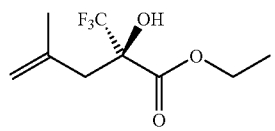

[7]

the method comprising reacting ethyl trifluoropyruvate represented by formula [4]

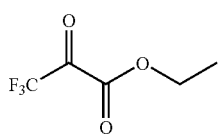

with isobutene represented by formula [5]

in the presence of 0.0003 moles or less of a bivalent cationic palladium complex having an optically active ligand relative to 1 mole of the ethyl trifluoropyruvate represented by formula [4] and in the presence of toluene as reaction solvent.

9. A method for producing an optically active, fluorine-containing, carbonyl-ene product represented by formula [3]

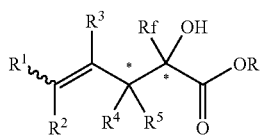

wherein Rf represents a perfluoroalkyl group,

R represents an alkyl group, each of $R^1$, $R^2$, $R^3$, $R^4$ and $R^5$ independently represents a hydrogen atom, alkyl group, substituted alkyl group, aromatic ring group, or substituted aromatic ring group,

* represents an asymmetric carbon but is not an asymmetric carbon in case that $R^4$ and $R^5$ are the same substituents, and wave line represents an E configuration or Z configuration in geometrical configuration of the double bond the method comprising reacting a fluorine-containing α-ketoester represented by formula [1]

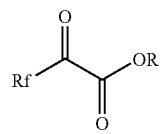

wherein Rf and R respectively represent the same substituents as above, with an alkene represented by formula [2]

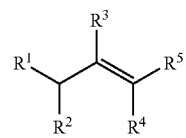

wherein each of $R^1$, $R^2$, $R^3$, $R^4$ and $R^5$ independently represents the same substituent as above, in the presence of a transition metal complex having an optically active ligand and in the presence of less than 1.0 L (liter) of a halogenated hydrocarbon-series reaction solvent relative to 1 mole of the fluorine-containing α-ketoester represented by formula [1].

10. A method according to claim 9, wherein usage of the transition metal complex having the optically active ligand is 0.001 moles or less relative to 1 mole of the fluorine-containing α-ketoester represented by formula [1].

* * * * *